(12) United States Patent
Leonhardt et al.

(10) Patent No.: US 10,405,778 B2
(45) Date of Patent: Sep. 10, 2019

(54) DEVICE FOR COMBINED RESPIRATORY GAS ANALYSIS AND LUNG FUNCTION TEST

(71) Applicant: Robert Bosch GmbH, Stuttgart (DE)

(72) Inventors: Ronny Leonhardt, Gerlingen (DE); Robert Giezendanner-Thoben, Gerlingen (DE); Cristian-Aurelian Coclici, Stuttgart (DE)

(73) Assignee: Robert Bosch GmbH, Stuttgart (DE)

( * ) Notice: Subject to any disclaimer, the term of this patent is extended or adjusted under 35 U.S.C. 154(b) by 990 days.

(21) Appl. No.: 14/782,817

(22) PCT Filed: Mar. 14, 2014

(86) PCT No.: PCT/EP2014/055126
§ 371 (c)(1),
(2) Date: Oct. 7, 2015

(87) PCT Pub. No.: WO2014/166697
PCT Pub. Date: Oct. 16, 2014

(65) Prior Publication Data
US 2016/0029924 A1 Feb. 4, 2016

(30) Foreign Application Priority Data
Apr. 8, 2013 (DE) .................. 10 2013 206 111

(51) Int. Cl.
*A61B 5/08* (2006.01)
*A61B 5/097* (2006.01)
(Continued)

(52) U.S. Cl.
CPC .............. *A61B 5/097* (2013.01); *A61B 5/082* (2013.01); *A61B 5/087* (2013.01); *A61B 5/09* (2013.01);
(Continued)

(58) Field of Classification Search
CPC .......... A61B 5/097; A61B 5/091; A61B 5/087; A61B 5/09; A61B 5/082; A61M 39/223; G01N 33/497
See application file for complete search history.

(56) References Cited

U.S. PATENT DOCUMENTS 5,739,412 A    4/1998  Stock et al.
8,192,367 B2*  6/2012  Myklebust ........ A61M 16/0858
                                                          600/538
2011/0072883 A1  3/2011  Abraham-Fuchs et al.

FOREIGN PATENT DOCUMENTS

CN      1455690 A    11/2003
CN    102188247 A     9/2011
(Continued)

OTHER PUBLICATIONS

International Search Report corresponding to PCT Application No. PCT/EP2014/055126, dated Nov. 3, 2014 (German and English language document) (7 pages).

*Primary Examiner* — Christian Jang
(74) *Attorney, Agent, or Firm* — Maginot, Moore & Beck LLP (57) ABSTRACT

A device for combined respiratory gas analysis and lung function test includes a gas quantity measuring device, a gas analysis device, and a multi-way valve configured for placement at least between a first valve path combination and a second valve path combination. A first gas path between the gas quantity measuring device and a second combined inlet/outlet opening is established while by-passing the gas analysis device with the first valve path combination of the multi-way valve, and a second gas path is established between a first combined inlet/outlet opening, the gas analysis device, the gas quantity measuring device, and the second combined inlet/outlet opening with the second valve path combination of the multi-way valve.

1 Claim, 7 Drawing Sheets

(51) Int. Cl.
*A61B 5/09* (2006.01)
*G01N 33/497* (2006.01)
*A61B 5/087* (2006.01)
*A61B 5/091* (2006.01)
*A61M 39/22* (2006.01)

(52) U.S. Cl.
CPC ............ *A61B 5/091* (2013.01); *A61M 39/223* (2013.01); *G01N 33/497* (2013.01)

(56) References Cited

FOREIGN PATENT DOCUMENTS

| DE | 10 2009 038 237 A1 | 3/2011 |
| DE | 10 2009 043 236 A1 | 4/2011 |
| WO | 2004/023997 A1 | 3/2004 |
| WO | 2013/003429 A1 | 1/2013 |

\* cited by examiner

DEVICE FOR COMBINED RESPIRATORY GAS ANALYSIS AND LUNG FUNCTION TEST

This application is a 35 U.S.C. § 371 National Stage Application of PCT/EP2014/055126, filed on Mar. 14, 2014, which claims the benefit of priority to Serial No. DE 10 2013 206 111.0, filed on Apr. 8, 2013 in Germany, the disclosures of which are incorporated herein by reference in their entirety.

The present disclosure relates to a device for combined respiratory gas analysis and lung function testing, to a method for combined respiratory gas analysis and lung function testing by means of such a device, and to a multiway valve for use in such a device.

BACKGROUND

Measuring devices for assisting the diagnosis and treatment of lung diseases are known from the prior art. In a known way, spirometers are used to assess lung function. Furthermore, respiratory gas analysis apparatuses for determining the NO concentration in respiratory air are known, for example, from WO 2004/023997. Because of the method requirements resulting from the medical analysis methods used, only special monofunctional apparatuses are conventionally used.

SUMMARY

The present disclosure relates to a device for combined respiratory gas analysis and lung function testing, comprising:
- a first combined inlet/outlet opening,
- a second combined inlet/outlet opening,
- a gas quantity measuring device for determining an amount of the respiratory gas flowing through,
- a gas analysis device for analyzing the respiratory gas,
- a multiway valve which can be brought at least between a first valve path combination and a second valve path combination.

A "combined inlet/outlet opening" is in this case intended, in particular, to mean an opening of the device which is used in at least a first operating state as an inlet opening for a gas and in at least a second operating state as an outlet opening for the gas.

It is proposed that
- with the first valve path combination of the multiway valve, while circumventing the gas analysis device, a first gas path can be established between the first combined inlet/outlet opening, the gas quantity measuring device and the second combined inlet/outlet opening, and
- with the second valve path combination of the multiway valve, a second gas path can be established between the first combined inlet/outlet opening, the gas analysis device, the gas quantity measuring device and the second combined inlet/outlet opening.

With an embodiment according to the disclosure of the device, it is possible both to carry out a lung function test and to determine individual respiratory gas concentrations. With a multiway valve, with a suitable configuration, it is possible to switch between two gas paths so that spirometry and gas analysis methods can be combined. This makes it possible to determine parameters of the lung function test and to determine parameters of the gas analysis within one measurement cycle, and by coupled evaluation the systematic accuracy of the method can be increased in comparison with individual measurements.

It is furthermore proposed that the gas quantity measuring device comprises a gas energy machine which can be used both as a driven machine and as a power engine. In this context, a "gas energy machine" is intended in particular to mean a turbomachine in which energy transmission between the gas and the turbomachine takes place in an open gas space. When the gas energy machine is used as a driven machine, energy is transmitted from the turbomachine to the gas. When the gas energy machine is used as a power engine, energy is transmitted from the gas to the turbomachine. The energy obtained in this case is used only for rotation of the turbomachine. The rotational speed in turn provides information about the volume flow which is forced through the gas energy machine.

The gas energy machine may therefore be used both to determine an amount of gas flowing through and to assist breathing of a patient to be examined by reducing the effective flow resistance in the measuring device.

The gas energy machine may advantageously comprise at least one impeller, which is arranged on a central shaft and which can be used as a fan during operation of the gas energy machine as a driven machine and can be used as a measuring turbine (gas volume flow sensor) during operation of the gas energy machine as a power engine.

It is furthermore proposed that the device has a gas conditioning device for modifying the chemical composition of the respiratory gas. In this way, possibilities for the gas analysis can be significantly widened, or conduct of the gas analysis can be simplified.

If the device has a gas volume flow sensor, then determination of an amount of gas flowing through the device per unit time can be achieved in a way which is particularly simple in terms of design.

It is furthermore proposed that the conversion between the first valve path combination and the second valve path combination can be carried out as a function of a predetermined period of time or a predetermined amount of gas which has flowed through. In this way, conduct of a combined respiratory gas analysis and lung function test can be adapted individually to patient conditions.

The present disclosure furthermore relates to a multiway valve for use in a device for combined respiratory gas analysis and lung function testing according to one of the embodiments and refinement disclosed above, or a combination thereof.

With suitable configuration, sealing and contamination problems can be avoided, or at least reduced.

It is proposed that the first valve path combination and the second valve path combination have a common gas inlet region and a common gas outlet region. In this way, with suitable configuration, a number of required multiway valves of the device can be reduced.

In a preferred embodiment, the multiway valve has a control device which comprises precisely one camshaft, wherein the conversion between the first valve path combination and the second valve path combination can be carried out by reversible rotation of the camshaft. In this case, the conversion may be carried out by a direct or indirect effect of at least two cams of the camshaft on the first or second gas path. By virtue of the restriction to precisely one camshaft, the multiway valve requires only one drive and can therefore be configured in a way which is particularly compact and saves on parts.

If the reversible rotation of the camshaft is carried out by means of a stepper motor, bistable and currentless functional settings of the multiway valve can be achieved.

It is furthermore proposed that the control device comprises at least a first resilient membrane and a second resilient membrane, which are arranged between the camshaft and one of the at least two valve path combinations and are intended to interact respectively with at least one cam of the camshaft in order to achieve the conversion between the first valve path combination and the second valve path combination. In this way, the conversion between the first valve path combination and the second valve path combination can be achieved in a way which is particularly simple in design terms and free of contamination.

A "resilient membrane" is in this case intended in particular to mean an essentially gas-impermeable body configured as a thin film, which consists essentially of a spring-elastic material. In particular, the spring-elastic material may be formed by an elastomer or a spring-elastic metal.

In a particularly advantageous configuration, the first resilient membrane and the second resilient membrane are configured in one piece. In this way, the design of the multiway valve can be configured particularly straightforwardly.

Another aspect of the disclosure is the provision of a method for combined respiratory gas analysis and lung function testing by means of a device for combined respiratory gas analysis and lung function testing according to one of the embodiments and refinements disclosed above, or a combination thereof.

The method comprises the following steps:
1. establishing the first gas path,
2. inhaling by flow of air from an external space through the second combined inlet/outlet opening along the first gas path in the direction of the first combined inlet/outlet opening,
3. exhaling for lung function testing in order for respiratory gas to flow through the gas quantity measuring device along the first gas path from the first combined inlet/outlet opening in the direction of the second combined inlet/outlet opening,
4. establishing the second gas path while carrying out step 3,
5. conducting the respiratory gas, which is flowing through, along the second gas path through the gas analysis device in the direction of the second combined inlet/outlet opening, and
6. flushing the gas analysis device by conducting air from the external space from the second combined inlet/outlet opening along the second gas path through the gas analysis device in the direction of the first combined inlet/outlet opening.

The method makes it possible to determine parameters of the lung function test and to determine parameters of the gas analysis within one measurement cycle, and by coupled evaluation the systematic accuracy of the method can be increased in comparison with individual measurements.

In another advantageous configuration, the method may involve repeated conduct of steps 1 to 5 before step 6 is carried out.

BRIEF DESCRIPTION OF THE DRAWINGS

Other advantages may be found in the following description of the drawing. The drawing represents an exemplary embodiment of the disclosure. The drawing, the description and the claims contain numerous features in combination. The person skilled in the art will also expediently consider the features individually and combine them to form further appropriate combinations.

DETAILED DESCRIPTION

Figure 1:
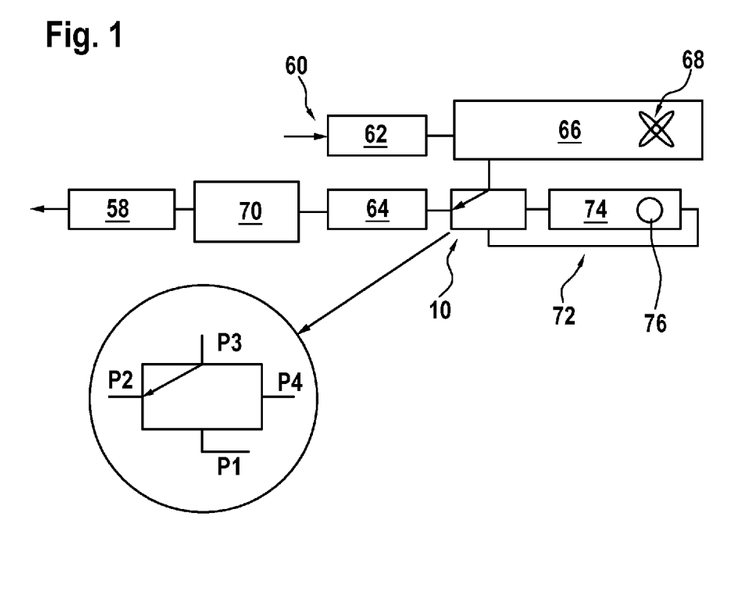
FIG. 1 shows a schematic representation of a device according to the disclosure for combined respiratory gas analysis and lung function testing in an operating state of an inhalation/breathing phase.

FIG. 1 shows a device according to the disclosure for combined respiratory gas analysis and lung function testing in a schematic representation. The device comprises a first combined inlet/outlet opening 58 and a second combined inlet/outlet opening 60.

The first combined inlet/outlet opening 58 is configured as a mouthpiece, and is intended to be placed by a subject with the end that faces toward the external space on the mouth, in order to allow easy inhalation through the device and easy exhalation into the device.

The second combined inlet/outlet opening 60 is configured as one access opening, facing toward the external space, of two access openings of an activated carbon filter 62.

Furthermore, the device comprises a gas conditioning device 64 for modifying the chemical composition of the respiratory gas, in which nitrogen monoxide NO from the respiratory gas is converted into nitrogen dioxide $NO_2$. The gas conditioning device 64 is pneumatically connected to an end, facing away from the external space, of the mouthpiece.

The device furthermore comprises a first gas quantity measuring device 66 for determining an amount of the respiratory gas flowing through, which comprises a gas energy machine configured as a fan 68. The fan 68 may be used as a power engine in order to determine an amount of a gas flow flowing through the device. The fan 68 may furthermore be used as a driven machine in order to facilitate inhalation for subjects with impaired breathing. In this case, an effective flow resistance in the measuring device is intended to be reduced.

For this case, the device may comprise a second gas quantity measuring device 70 configured as a gas mass flow sensor for pneumatic connection between the mouthpiece and the gas conditioning device 64.

The device furthermore contains a gas analysis device 72 for analyzing the respiratory gas. The gas analysis device 72 comprises a measurement chamber 74 with a respiratory analysis sensor 76 arranged therein.

As a central component, the device comprises a multiway valve 10. The multiway valve 10 comprises four pneumatic connections P1, P2, P3, P4. A first pneumatic connection P1 and a fourth pneumatic connection P4 of the multiway valve 10 are each connected by one end to the measurement chamber 74. A second pneumatic connection P2 of the multiway valve 10 is pneumatically connected to an end, facing away from the mouthpiece, of the gas conditioning device 64. A third pneumatic connection P3 of the multiway valve 10 is pneumatically connected to an end, facing away from the activated carbon filter 62, of the first gas quantity measuring device 66.

The multiway valve 10 can be converted reversibly between a first valve path combination A and a second valve path combination B. In FIG. 1, the multiway valve 10 is represented in the first valve path combination A, with which by rotating the gas analysis device 72 a first gas path can be established between the first combined inlet/outlet opening 58, the gas quantity measuring device 66 and the second combined inlet/outlet opening 60.

In this arrangement, the device is prepared for an operating state of an inhalation/breathing phase: one path of the gas flow extends from the external space through the activated carbon filter 62, the first gas quantity measuring device 66, the multiway valve 10, the gas conditioning device 64 and the second gas quantity measuring device 70, via the mouthpiece into the subject's lung. The fan 68 may be used to assist breathing by reducing the effective flow resistance of the device as a driven machine. The measurement chamber 74 lies pneumatically outside the first gas path.

In the inhalation/breathing phase, the inhalation takes place by air flowing in from the external space through the second combined inlet/outlet opening 60 along the first gas path in the direction of the first combined inlet/outlet opening 58.

Figure 2:
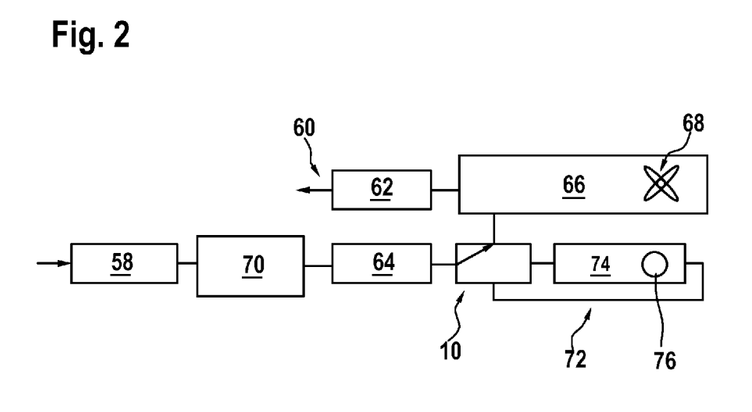
FIG. 2 shows a schematic representation of the device according to FIG. 1 in an operating state of a lung function testing phase.

FIG. 2 shows a schematic representation of the device according to FIG. 1 in an operating state of a lung function testing phase. The multiway valve 10 is still in the first valve path combination A, with which the first gas path is established.

The exhalation for the lung function testing takes place by respiratory gas from the subjects' lung flowing through the mouthpiece, through the second gas quantity measuring device 70, the gas conditioning device 64, the first gas quantity measuring device 66 and the activated carbon filter 62, along the first gas path from the first combined inlet/outlet opening 58 in the direction of the second combined inlet/outlet opening 60.

During a respiratory gas analysis, the inhalation in the operating state of an inhalation/breathing phase takes place similarly as during the lung function testing. The exhalation for the respiratory gas analysis takes place in the first phase by respiratory gas from the subjects' lung flowing through the mouthpiece, through the second gas quantity measuring device 70, the gas conditioning device 64, the first gas quantity measuring device 66 and the activated carbon filter 62, along the first gas path from the first combined inlet/outlet opening 58 in the direction of the second combined inlet/outlet opening 60.

Figure 3:
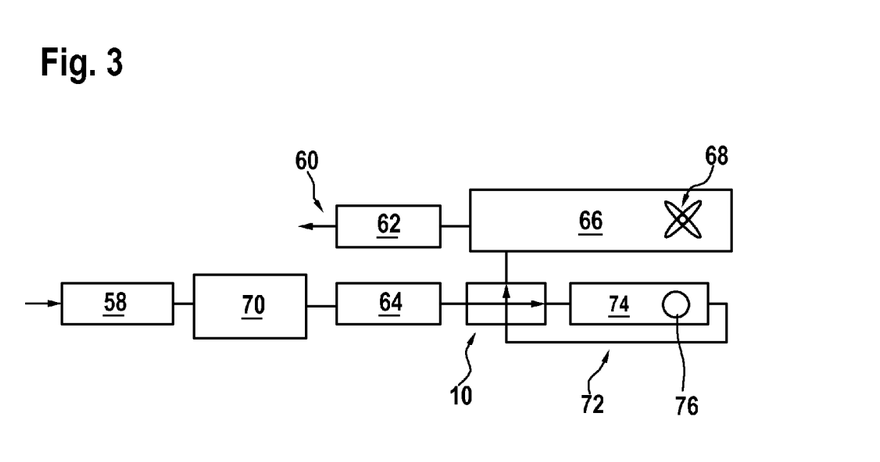
FIG. 3 shows a schematic representation of the device according to FIG. 1 in a third operating state of a respiratory gas analysis phase.

In a second phase of the respiratory gas analysis, by driving, the multiway valve 10 is brought from the first valve path combination A to the second valve path combination B, with which a second gas path can be established between the first combined inlet/outlet opening 58, the second gas quantity measuring device 70, the gas conditioning device 64, the gas analysis device 72, the first gas quantity measuring device 66, the activated carbon filter 62 and the second combined inlet/outlet opening 60. The multiway valve 10 may in this case be brought into the second valve path combination B selectively as a function of a predeterminable period of time or a predeterminable amount of gas which has flowed through.

In this operating state, which is represented in FIG. 3, the device is prepared for carrying out a respiratory gas analysis phase. In this case, the respiratory gas flowing through is conducted along the second gas path from the first combined inlet/outlet opening 58, through the gas analysis device 72 in the direction of the second combined inlet/outlet opening 60.

Figure 4:
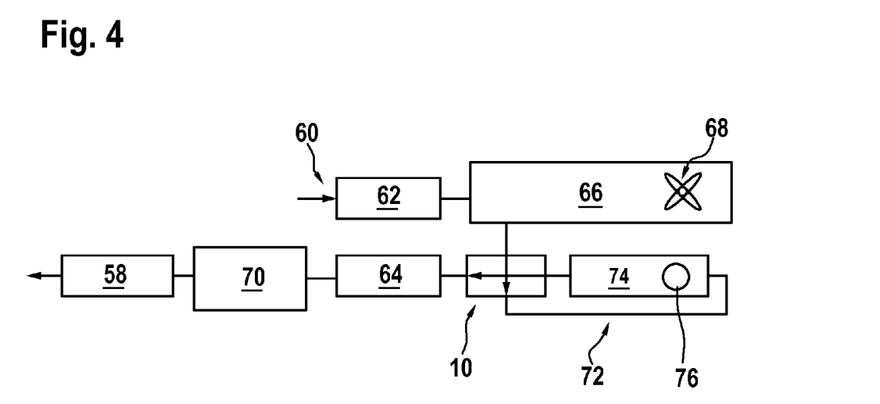
FIG. 4 shows a schematic representation of the device according to FIG. 1 in a fourth operating state of a flushing phase.

After the end of the respiratory gas analysis phase, which is indicated to the subject by an acoustic signal of a control apparatus (not represented), the gas analysis device 72 is flushed by conducting air from the external space from the second combined inlet/outlet opening 60 along the second gas path, through the gas analysis device 72 in the direction of the first combined inlet/outlet opening 58, the fan 68 being used as a driven machine. FIG. 4 schematically represents the device in the operating state of the flushing phase.

The structure and function of the multiway valve 10 as a central component of the device according to FIG. 1 will be explained with the aid of FIGS. 5 to 10.

Figure 5:
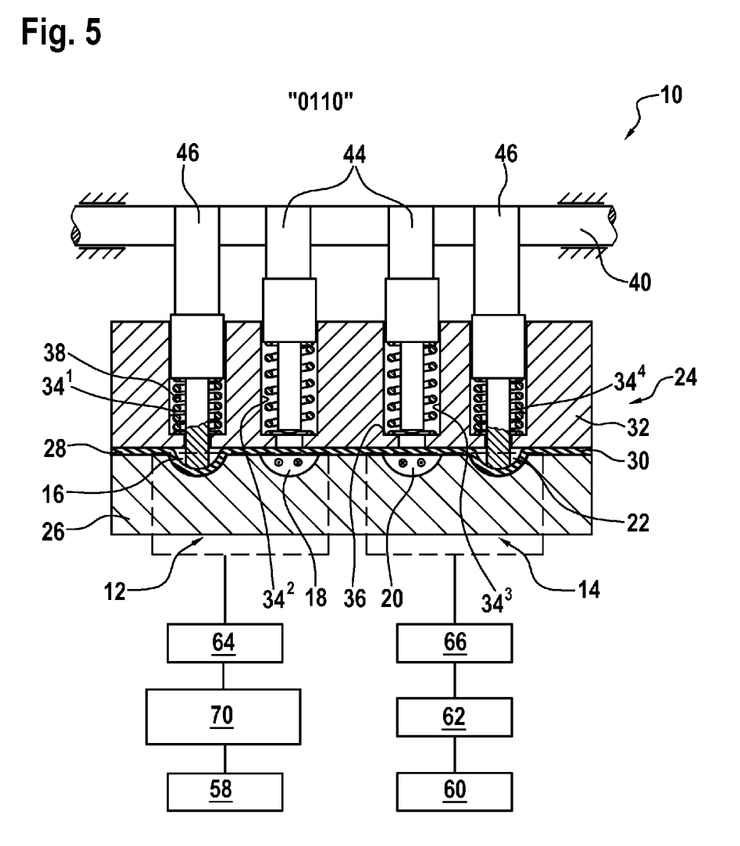
FIG. 5 shows a schematized sectional view of a multiway valve according to the disclosure of the device according to FIG. 1 in a state of a first valve path combination.

FIG. 5 shows a schematized sectional view of the multiway valve 10 of the device according to FIG. 1 in a state of the first valve path combination A.

The multiway valve 10 has a gas inlet region 12 and a gas outlet region 14. The gas inlet region 12 is continued in the interior of the multiway valve 10 in a first channel 16 and a second channel 18, which are arranged separately from one another in a channel block 26 in the vicinity of the gas inlet region 12. The gas outlet region 14 is likewise continued in the interior of the multiway valve 10 in a third channel 20 and a fourth channel 22, which extend separately from one another in the channel block 26 in the vicinity of the gas outlet region 14.

A control device 24 is used for the conversion of the multiway valve 10 between the first valve path combination A and the second valve path combination B.

The control device 24 comprises a first resilient membrane 28, which is used as a cover of the two channels 16, 18 of the gas inlet region 12, and a second resilient membrane 30, which is used as a cover of the two channels 20, 22 of the gas outlet region 14. The first resilient membrane 28 and the second resilient membrane 30 are configured in one piece, although in principle they may also be formed as separate membranes.

The first resilient membrane 28 and the second resilient membrane 30 are covered, on the side facing away from the channel block 26, by a cover block 32, which is equipped with four cylindrical guides $34^1$-$34^4$ arranged perpendicularly to the resilient membranes 28, 30, one of the guides $34^1$-$34^4$ respectively being arranged above one of the channels 16, 18, 20, 22. Each of the guides $34^1$-$34^4$ has, at an end facing toward the resilient membranes 28, 30, a counter-bearing 36 for supporting a spring element configured as a coil spring 38.

Figure 6:
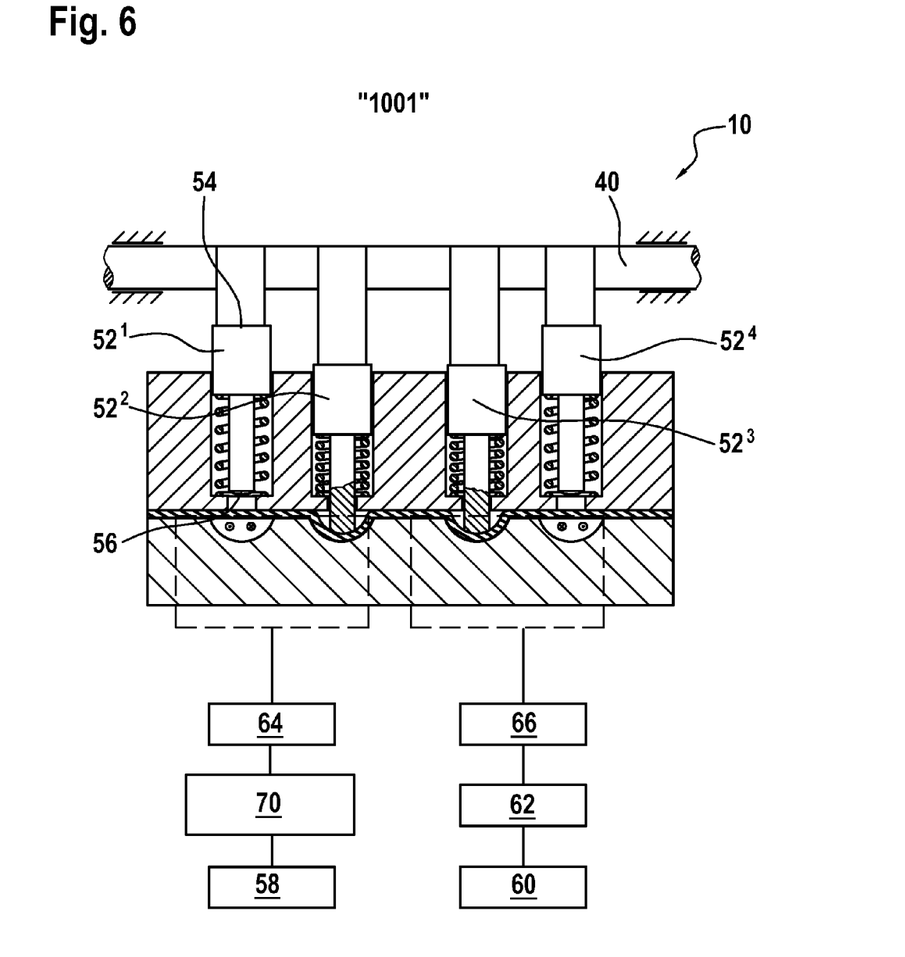
FIG. 6 shows the multiway valve according to FIG. 5 in the same view in a state of a second valve path combination.

The control device 24 comprises precisely one camshaft 40 with four cam units 44, 46 arranged on the camshaft 40. The camshaft 40 is arranged above the cover block 32 and parallel to the two resilient membranes 28, 30. Four plungers $52^1$-$52^4$ configured as individual pins are arranged below the camshaft 40 (FIG. 6). Each of the cylindrical plungers 52$^1$-52$^4$ has a first end 54, matched to the diameter of the guide 34 as a header element, and a second end 56 matched to an internal diameter of the coil spring 38, as well as an extent direction between the two ends 54, 56, which in a state ready for operation is oriented perpendicularly to the two resilient membranes 28, 30. The plungers 52$^1$-52$^4$ are intended to execute linear movements, parallel to the respective extent direction, in the guides 34$^1$-34$^4$ of the cover block 32.

In the state ready for operation, because of the spring force of the coil springs 38, the upper sides of the head ends of the plungers 52$^1$-52$^4$ come to bear in a spring-loaded fashion with the cams 48$^1$-48$^4$, 50$^1$-50$^4$ of the cam units 44, 46.

The second ends 56 of the plungers 52$^1$-52$^4$ are configured with a radius of curvature which is matched to the cross-shape of the channels 16, 18, 20, 22. The plungers 52$^1$-52$^4$ are intended, by means of one of the cams 48$^1$-48$^4$, 50$^1$-50$^4$ of the camshaft 40, to execute a linear movement parallel to the extent direction in the direction of one of the two resilient membranes 28, 30 against the spring force of one of the coil springs 38 within one of the guides 34$^1$-34$^4$ of the cover block 32 in order to respectively seal one of the channels 16, 18, 20, 22 by means of the second end 56 of the plunger 52$^1$-52$^4$ and because of the resilient property of the membranes 28, 30. The effect achieved by this embodiment is that a fluid space intended for conducting the respiratory gas is pneumatically fully leaktight, and direct contact with the plungers 52$^1$-52$^4$ of the control device 24 can be avoided.

On a side facing away from the gas inlet region 12, or the gas outlet region 14, of the multiway valve 10, the second channel 18 and the third channel 20 are pneumatically connected to one another. Furthermore, the first channel 16 is pneumatically connected on a side facing away from the gas inlet region 12 to one end of the measurement chamber 74, and the fourth channel 22 is pneumatically connected on a side facing away from the gas outlet region 14 to the other end of the measurement chamber 74.

Figure 7:
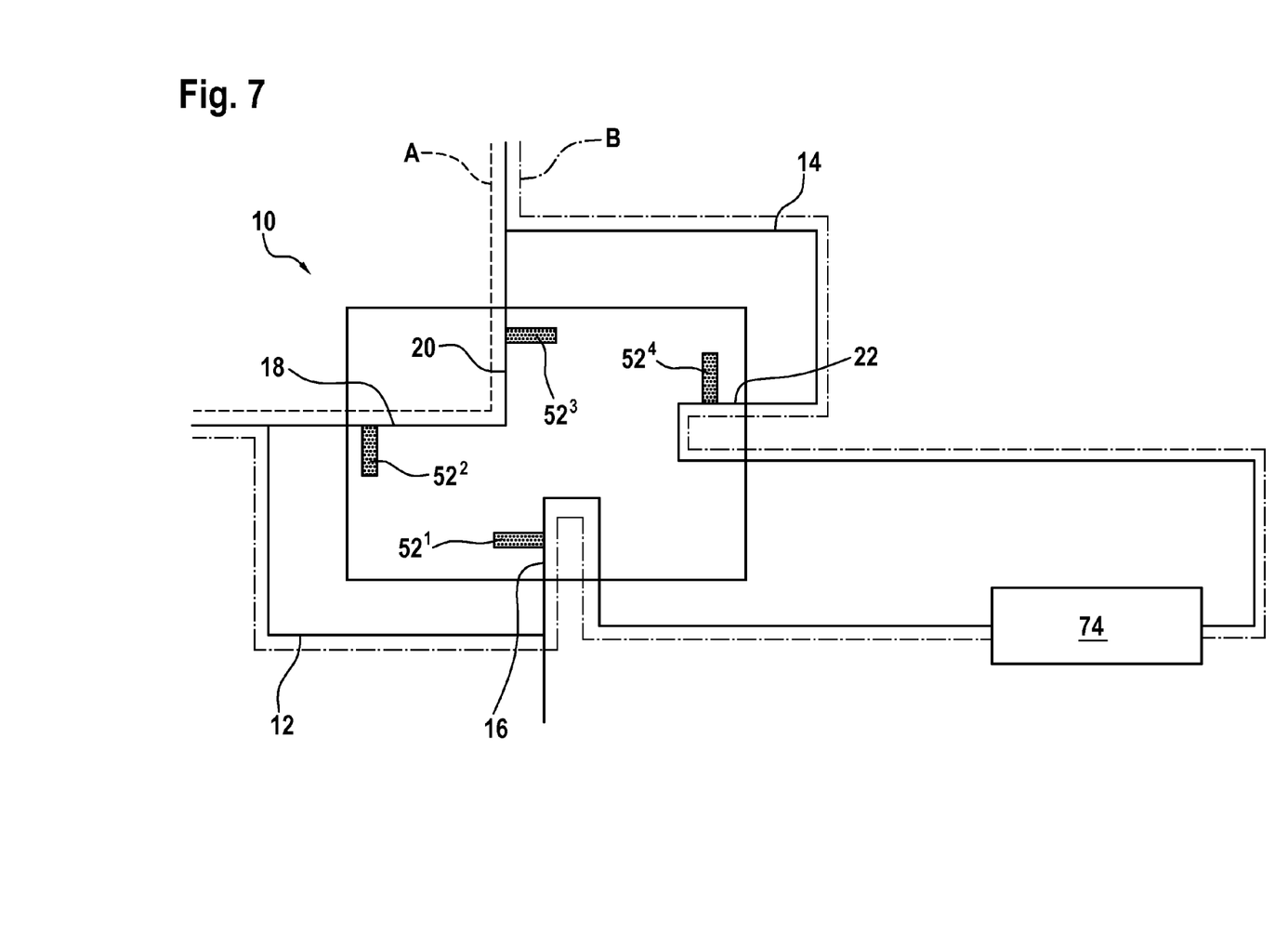
FIG. 7 shows a schematized representation of the pneumatic connections of the multiway valve according to FIGS. 5 and 6.

For illustration, FIG. 7 illustrates a schematized representation of the pneumatic connections of the channels 16, 18, 20, 22 and the arrangement of the plungers 52$^1$, 52$^4$ within the multiway valve 10.

The first valve path combination A, represented in FIG. 5, is characterized in that the cams 48$^1$-48$^4$, 50$^4$-50$^4$ of the camshaft 40 and their rotation position are configured in such a way that the first channel 16 is sealed by means of the first plunger 52$^1$ and the first membrane 28, and the fourth channel 22 is sealed by means of the fourth plunger 52$^4$ and the second membrane 30 and the second channel 18 and the third channel 20 are open.

The first valve path combination A shown in FIG. 5 is indicated by a dashed line in FIG. 7.

FIG. 6 shows a schematized sectional view of the multiway valve 10 in a state of the second valve path combination B. The multiway valve 10 can be brought from the first valve path combination A to the second valve path combination B by reversible rotation of the camshaft 40.

The second valve path combination B is characterized in that the cams 48$^1$-48$^4$, 50$^1$-50$^4$ of the camshaft 40 and their rotation position are configured in such a way that the second channel 18 is sealed by means of the second plunger 52$^2$ and the first membrane 28 and the third channel 20 is sealed by means of the third plunger 52$^3$ and the second membrane 30, and the first channel 16 and the fourth channel 22 are open.

The second valve path combination B shown in FIG. 6 is indicated by a dot-and-dash line in FIG. 7. As can be seen in FIG. 7, the first valve path combination A and the second valve path combination B comprise the common gas inlet region 12 and the common gas outlet region 14.

Figure 8:
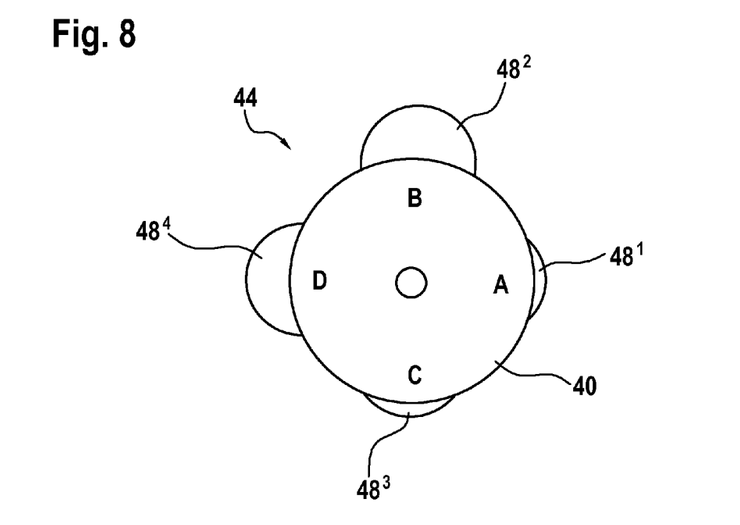
FIG. 8 shows a first embodiment of a cam unit of a camshaft of the multiway valve according to FIGS. 5 and 6.

FIG. 8 shows an embodiment of the cam unit 44 of the camshaft 40, one cam unit 44 each being provided in order to drive the second plunger 52$^2$ and the third plunger 52$^3$. Four cams 48$^1$-48$^4$ are arranged in the cam unit 44 at a uniform angular separation of 90° with respect to the camshaft 40, so that the multiway valve 10 can be brought from one valve path combination A, B, C, D to another valve path combination A, B, C, D by reversible rotation of the camshaft 40 through 90°, four different positions of the camshaft 40, corresponding to the four different valve path combinations A, B, C, D of the multiway valve 10, being possible. The cams 48$^1$-48$^4$ for driving the second plunger 52$^2$ and the third plunger 52$^3$ may, as an alternative, also be configured in one piece.

Figure 9:
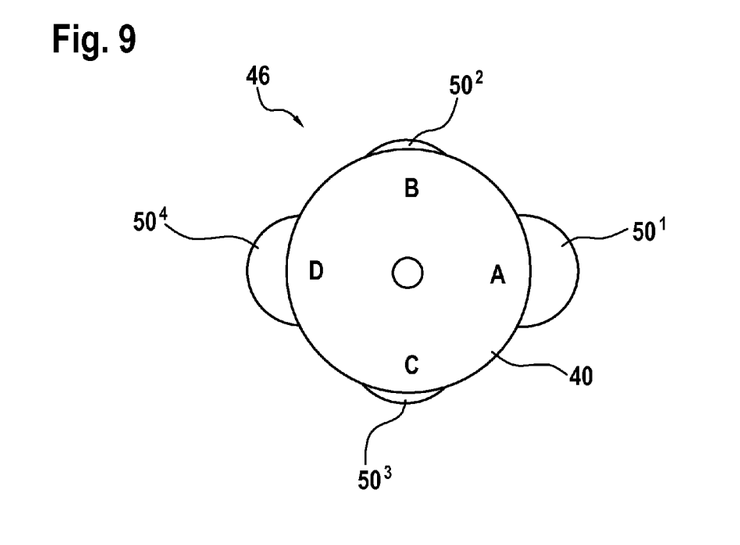
FIG. 9 shows a second embodiment of a cam unit of a camshaft of the multiway valve according to FIGS. 5 and 6.

FIG. 9 shows an embodiment of the cam unit 46 of the camshaft 40, one cam unit 46 each being provided in order to drive the first plunger 52$^1$ and the fourth plunger 52$^4$. Four cams 50$^1$-50$^4$ are in this case also arranged at a uniform angular separation of 90° with respect to the camshaft 40.

The flatter cams 48$^1$, 48$^3$, 50$^2$, 50$^3$ represented in FIGS. 8 and 9 make it possible to raise the plungers 52$^1$-52$^4$ arranged underneath, driven by the spring force of the corresponding coil springs 38, from the resilient membranes 28, 30 and release the channels 16, 18, 20, 22 lying below the resilient membranes 28, 30. The higher cams 48$^2$, 48$^4$, 50$^1$, 50$^4$ represented in FIGS. 8 and 9 are configured in order to force the plungers 52$^1$-52$^4$ arranged underneath against the spring force of the coil springs 38 in a linear movement in the direction of the resilient membrane 28, 30 and seal the channel 16, 18, 20, 22 lying below the resilient membrane 28, 30. The first resilient membrane 28 and the second resilient membrane 30, arranged between the camshaft 40 and the valve path combinations A, B, C, D, are intended to cooperate respectively with at least one of the cams 48$^1$-48$^4$, 50$^1$-50$^4$ of the camshaft 40 in order to achieve conversion of the multiway valve 10 between a first of the valve path combinations A, B, C, D and a second of the valve path combinations A, B, C, D.

The reversible rotation of the camshaft 40 may be carried out by hand. As an alternative, however, it may also be achieved by a stepper motor (not represented), multistable and currentless valve path combinations A, B, C, D of the multiway valve 10 being achievable.

The possible positions of the plungers 52$^1$-52$^4$ may, for simplicity, be denoted by indicating a binary number. In this case, the binary number "0" denotes a position of a plunger 52$^1$-52$^4$ in which a channel 16, 18, 20, 22 arranged below the plunger 52$^1$-52$^4$ is sealed. The binary number "1" is intended to denote an open channel 16, 18, 20, 22.

The first valve path combination A shown in FIG. 5 may accordingly be denoted by the binary number "0110". The second valve path combination B shown in FIG. 6 corresponds to the binary number "1001".

With the cams 48$^1$-48$^4$, 50$^4$-50$^4$, represented in FIGS. 8 and 9, of the cam units 44, 46, the following further valve path combinations are obtained: —C—"1111" (all channels 16, 18, 20, 22 open; maintenance position) —D—"0000" (all channels 16, 18, 20, 22 closed; storage position).

Figure 10:
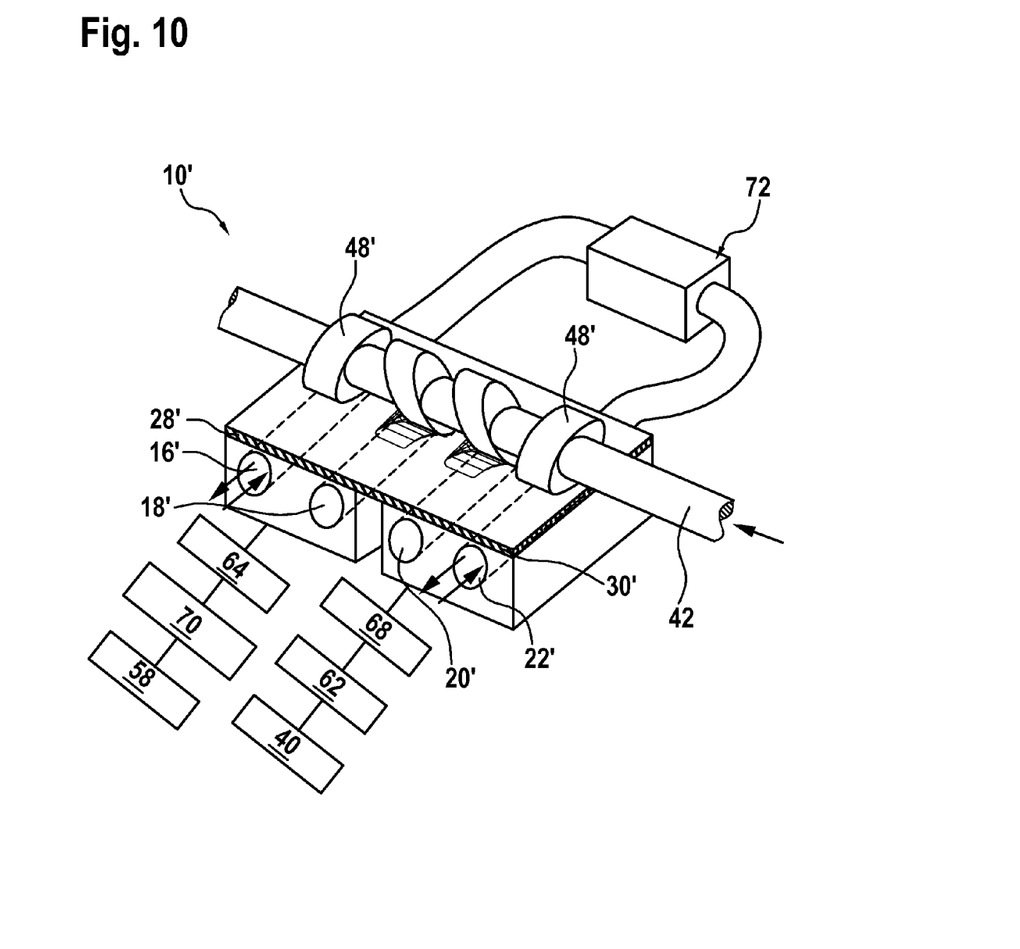
FIG. 10 shows an alternative embodiment of a multiway valve in a schematized perspective view.

FIG. 10 shows an alternative embodiment of a multiway valve 10' in a schematized perspective view. Unlike in the first embodiment, the plungers and the cover block together with the guides and coil springs are omitted here, so that cams 48', 50' arranged on a camshaft 42 are intended to mechanically act directly on a first resilient membrane 28' and a second resilient membrane 30' in such a way that a channel 16', 18', 20', 22', arranged below the cam 48', 50' and one of the membranes 28', 30', of the multiway valve 10' can be sealed in a gas-tight fashion and can be opened again by further reversible rotation of the camshaft 42.

The invention claimed is:

1. A method for combined respiratory gas analysis and lung function testing by a device including a first combined inlet/outlet opening, a second combined inlet/outlet opening, a gas quantity measuring device, a gas analysis device, and a multiway valve configured to be brought at least between a first valve path combination and a second valve path combination, the method comprising:
  establishing a first gas path between the first combined inlet/outlet opening, the gas quantity measuring device, and the second combined inlet/outlet opening with the first valve path combination of the multiway valve while circumventing the gas analysis device;
  inhaling by flow of air from an external space outside the gas analysis device, through the second combined inlet/outlet opening along the first gas path in a direction of the first combined inlet/outlet opening;
  exhaling for lung function testing in order for respiratory gas to flow through the gas quantity measuring device along the first gas path from the first combined inlet/outlet opening in a direction of the second combined inlet/outlet opening;
  establishing the second gas path while exhaling for lung function testing, the second gas path established between the first combined inlet/outlet opening, the gas analysis device, the gas quantity measuring device, and the second combined inlet/outlet opening with the second valve path combination of the multiway valve;
  conducting the respiratory gas flowing through along the second gas path through the gas analysis device in the direction of the second combined inlet/outlet opening; and
  flushing the gas analysis device by conducting air from the external space outside the gas analysis device, through the second combined inlet/outlet opening along the second gas path through the gas analysis device in the direction of the first combined inlet/outlet opening.

* * * * *